(12) United States Patent
Fisker et al.

(10) Patent No.: US 9,861,457 B2
(45) Date of Patent: Jan. 9, 2018

(54) SYSTEM AND METHOD FOR EFFECTIVE PLANNING, VISUALIZATION, AND OPTIMIZATION OF DENTAL RESTORATIONS

(75) Inventors: Rune Fisker, Virum (DK); Karl-Josef Hollenbeck, København Ø (DK); Sune Jørgensen, Roskilde (DK); Tais Clausen, Klagshamn (SE)

(73) Assignee: 3SHAPE A/S, Copenhagen (DK)

( * ) Notice: Subject to any disclaimer, the term of this patent is extended or adjusted under 35 U.S.C. 154(b) by 1219 days.

(21) Appl. No.: 13/256,452

(22) PCT Filed: Mar. 18, 2010

(86) PCT No.: PCT/DK2010/050063
§ 371 (c)(1),
(2), (4) Date: Dec. 6, 2011

(87) PCT Pub. No.: WO2010/105628
PCT Pub. Date: Sep. 23, 2010

(65) Prior Publication Data
US 2012/0095732 A1    Apr. 19, 2012

Related U.S. Application Data

(60) Provisional application No. 61/161,903, filed on Mar. 20, 2009.

(51) Int. Cl.
A61C 13/00 (2006.01)

(52) U.S. Cl.
CPC ............ *A61C 13/0004* (2013.01)

(58) Field of Classification Search
None
See application file for complete search history.

(56) References Cited

U.S. PATENT DOCUMENTS

| 5,775,912 A | 7/1998 | Panzera et al. |
| 6,049,743 A | 4/2000 | Baba |
| 6,431,870 B1 | 8/2002 | Sachdeva |
| 6,587,828 B1 | 7/2003 | Sachdeva |

(Continued)

FOREIGN PATENT DOCUMENTS

| JP | H09-010232 A | 1/1997 |
| JP | 10-75963 A | 3/1998 |

(Continued)

OTHER PUBLICATIONS

Beuer, F.; Schweiger, J. & Edelhoff, D. "Digital Dentistry: An Overview of Recent Developments for CAD/CAM Generated Restorations" British Dental Journal, vol. 204, No. 9, pp. 505-511 (2008).*

(Continued)

*Primary Examiner* — Jay B Hann
(74) *Attorney, Agent, or Firm* — Buchanan Ingersoll & Rooney PC

(57) ABSTRACT

A method for planning, visualizing, and/or optimizing dental restoration on the pre-prepared teeth of a patient. The method includes obtaining 3D digital models of the pre-prepared teeth and the prepared teeth, and aligning these 3D models. A CAD model of a dental restoration for the prepared teeth is designed based on the 3D digital model of the pre-prepared teeth.

20 Claims, 6 Drawing Sheets

(56) References Cited

U.S. PATENT DOCUMENTS

| | | | |
|---|---|---|---|
| 6,786,726 B2 | 9/2004 | Lehmann et al. | |
| 7,110,594 B2* | 9/2006 | Jones et al. | 433/24 |
| 7,133,042 B2* | 11/2006 | Anh et al. | 433/24 |
| 7,796,811 B2* | 9/2010 | Orth et al. | 382/154 |
| 8,425,229 B2* | 4/2013 | Nilsson et al. | 433/213 |
| 8,454,365 B2* | 6/2013 | Boerjes et al. | 433/223 |
| 8,706,672 B2* | 4/2014 | Malfliet et al. | 706/47 |
| 2003/0207227 A1* | 11/2003 | Abolfathi | 433/24 |
| 2004/0015327 A1 | 1/2004 | Sachdeva et al. | |
| 2004/0197727 A1 | 10/2004 | Sachdeva et al. | |
| 2005/0070782 A1* | 3/2005 | Brodkin | 433/201.1 |
| 2005/0271996 A1 | 12/2005 | Sporbert et al. | |
| 2006/0063135 A1* | 3/2006 | Mehl | 433/213 |
| 2008/0064008 A1* | 3/2008 | Schmitt | 433/140 |
| 2008/0090207 A1 | 4/2008 | Rubbert | |
| 2008/0153061 A1 | 6/2008 | Marcello | |
| 2008/0286722 A1 | 11/2008 | Berckmans et al. | |
| 2009/0068617 A1 | 3/2009 | Lauren | |

FOREIGN PATENT DOCUMENTS

| | | |
|---|---|---|
| JP | 11-128248 A | 5/1999 |
| JP | 2002-272763 | 9/2002 |
| JP | 2004-536662 A | 12/2004 |
| WO | 03/011165 A1 | 2/2003 |
| WO | WO 2004/098378 A2 | 11/2004 |
| WO | WO 2006/065955 A2 | 6/2006 |
| WO | WO 2007/117239 A1 | 10/2007 |
| WO | 2008-128700 A1 | 10/2008 |
| WO | 2008/145293 A2 | 12/2008 |
| WO | WO 2009/091438 A1 | 7/2009 |

OTHER PUBLICATIONS

Hassan et al., "A Volumetric 3D Model of the Human Jaw" International Congress Series, (2005), vol. 1281, pp. 1244-1249.

Zhao et al., "Multimodal Registration of Dental and Facial Images" Proceeding of the 6th LASTED International Conference Signal and Image Processing, Aug. 23-25, 2004, Honolulu, Hawaii, USA, pp. 401-406.

Office Action (Notice of Reasons for Rejection) dated Feb. 4, 2014, by the Japanese Patent Office in corresponding Japanese Patent Application No. 2012-500069. (8 pages).

Office Action issued in corresponding Chinese Patent Application No. 201080022163.X, dated Dec. 30, 2013, and English Translation thereof.

Rangel et al., "Integration of digital dental casts in 3-dimensional facial photographs", American Journal of Orthodontics and Dentofacial Orthopedics, Dec. 2008, pp. 820-826, vol. 134, No. 6.

Pinheiro et al., "A Computational Method for Recording and Analysis of Mandibular Movements", Journal of Applied Oral Science, 2008, pp. 321-327, vol. 16, No. 5.

Callieri et al., "Reconstructing textured meshes from multiple range+rgb maps", VMV 2002.

Ahmad, "Anterior dental aesthetics: Facial perspective", British Dental Journal, Jul. 2005, pp. 15-21, vol. 199, No. 1.

Ackerman et al., "Smile Analysis and Design in the Digital Era", JCO, 2002, pp. 221-236, vol. 16, No. 4.

Xia et al., "Computer-assisted three-dimensional surgical planning and simulation: 3D color facial model generation", International Journal of Oral & Maxillofacial Surgery, 2000, pp. 2-10, vol. 29.

Xia et al., Computer-assisted three-dimensional surgical planning and simulation, International Journal of Oral & Maxillofacial Surgery, 2000, pp. 250-258, vol. 29.

International Search Report (PCT/ISA/210) dated Sep. 9, 2010, by Danish Patent Office as the International Searching Authority for International Application No. PCT/DK2010/050063.

Written Opinion (PCT/ISA/237) dated Sep. 9, 2010, by Danish Patent Office as the International Searching Authority for International Application No. PCT/DK2010/050063.

An English Translation of the Office Action (Notice of Reasons for Rejection) dated Mar. 17, 2015, in corresponding Japanese Patent Office Application No. 2012-500069 (9 pages).

* cited by examiner

| Step | Model number | Model graphic |
|---|---|---|
| 1 | 100 | |
| 2 | 101 | |
| 6 Margin line | | |
| 8 Designed restoration | 300 (gingiva for reference only) | |
| 9 | 400 | |
| 11 | 300, 400 aligned (101 not shown for clarity) | |
| 12 | 301 (gingiva for reference only) | |

Figure 6

SYSTEM AND METHOD FOR EFFECTIVE PLANNING, VISUALIZATION, AND OPTIMIZATION OF DENTAL RESTORATIONS

FIELD OF THE INVENTION

The present invention relates to a system and a method for planning dental restorative work. The invention furthermore relates to a system and a method for interactive CAD design and realistic 3D presentation and visualization of dental restorations and subsequent physical realization by means of CAM.

BACKGROUND OF THE INVENTION

In dental practice, diagnostic wax-ups are created to visualize and plan restorative treatment, e.g., veneers or crowns on the anterior/front teeth. Diagnostic wax-ups are traditionally created in wax on gypsum casts by the dental laboratory for the dentist who uses it for treatment planning as well as for visualization and discussion of the restorative result with the patient. The dialog between dentist and patient is an important tool for improved patient satisfaction and often enables more expensive treatments. To transfer the design from the diagnostic wax-up to the patient's teeth, the dental technician typically looks at the original diagnostic wax-up and manually tries to replicate this design for the real restorations, incorporating potential comments from the dentist and the patient. This manual replication process is both costly, possibly inaccurate, and time consuming.

Because of the manual labor involved, diagnostic wax-ups are generally expensive, often several hundred US dollars. Creating a wax-up model is also time-consuming, such that the patient generally has to return for another appointment to evaluate it. Because diagnostic wax-ups are models of teeth only, they also fail to convey the full aesthetic impact of a restorative treatment. The visual impression of a patient's smile is also determined by the gingiva and the entire face [1]. Furthermore, a free standing wax-up model cannot convey the lighting to which teeth are subject to inside the mouth. In the field of orthodontics, treatment planning has more commonly involved 3D models of both the teeth and the face, or even the head. Data sources include 2D color pictures of the face and CT scans of the head [2, 3].

WO 2006/065955 discloses methods and systems for orthodontic treatment including a method for generating a photo-realistic image of a predicted result of a dental treatment on a patient, the method comprising: acquiring one or more images of the patient's pre-treatment face and teeth; generating a 3D digital model of the patient's pre-treatment face and teeth from the images of the patient's pre-treatment face and teeth; acquiring a 3D digital model of the patient's pre-treatment tooth arch; acquiring a 3D digital model of the patient's predicted tooth arch resulting from the treatment; generating a 3D digital model of the patient's predicted face and teeth from the 3D digital models of the patient's pre-treatment face and teeth, pre-treatment tooth arch, and predicted tooth arch; and rendering a photo-realistic image from the 3D digital model of the patient's predicted face and teeth.

WO 2004/098378 relates to orthodontic treatment and discloses a system for use in diagnosis and planning treatment of a human patient, comprising: a general purpose computer system having a processor and a user interface; a memory accessible to said general purpose computer system storing a) a first set of digital data representing patient craniofacial image information obtained from a first imaging device, and b) a second set of digital data representing patient craniofacial image information obtained from a second image device different from said first image device, said first and second sets of data representing at least in part common craniofacial anatomical structures of said patient, at least one of said first and second sets of digital data including data representing the external visual appearance or surface configuration of the face of the patient; and a set of computer instructions stored on a machine readable storage medium accessible to said general purpose computer system, wherein said set of instructions comprises instructions for causing said general computer system to: 1) automatically, and/or with the aid of operator interaction, superimpose said first set of digital data and said second set of digital data so as to provide a composite, combined digital representation of said craniofacial anatomical structures in a common coordinate system; 2) displaying said composite, combined digital representation of said craniofacial anatomical structures to a user of said system.

Thus, in the field of orthodontics, treatment planning involving 3D models of both the teeth and the face are known.

US 2008/153061 discloses a method for planning and performing dental treatments, comprising: an acquisition phase of a set of data relating to the position, to the conformation and to the dimension of at least one site inside the oral cavity of a patient who has to undergo a dental treatment and relating to the conformation of at least one portion of the face of said patient; a design phase of a virtual prototype of at least one dental prosthesis that can be fitted at said site during said treatment starting from said set of data and by means of a software program implemented on a computer; a determination phase, by means of said software program and starting from said set of data and from said virtual prototype of the dental prosthesis, of at least one virtual model suitable for visually reproducing said portion of the face following the fitting of said dental prosthesis; a preparation phase of said site by means of a dental instrument, with the assistance of said software and starting from said virtual prototype of the dental prosthesis and from said virtual model, before the installation and the manufacture of said dental prosthesis.

US 2008/153061 does not describe how to combine the various sources of geometry information, especially of the teeth, which are represented in both the scan of the face and that of the oral cavity. Neither does US 2008/153061 describe how to transfer the results of the design phase to the actual post-preparation dental geometry. Furthermore, US 2008/153061 assumes the reading phase of the virtual impression to be performed by the same dental instrument that executed the preparation of the oral site.

WO 2009/091438 discloses a method for designing a custom dental device, comprising the steps of: obtaining a set of time-based 3-dimensional images of the oral anatomy of a person during jaw motion; obtaining 3-dimensional data of a dental object of the person; registering the 3-dimensional data of the dental object to at least one of the time-based 3-dimensional images; using the time-based 3-dimensional images and registered 3-dimensional data to design a dental device.

WO 2009/091438 assumes that the 3-dimensional images be acquired at a rate of 50 per second; however, no such scanner exists at present nor is it disclosed. Furthermore, it appears unrealistic that the supposedly required accuracy of tracking dental objects, where the accuracy is about 20 m, can be achieved with any of the technologies referenced, nor is any new appropriate technology disclosed.

In all, it remains a problem to provide improved systems and methods for planning and visualizing dental restorations on teeth of a patient.

SUMMARY OF THE INVENTION

Dental restorations, both indirect restorations and e.g. partial dentures and implant-retained structures are more and more often designed using CAD software and a digital model of the patient's teeth, a digital model usually obtained by means of a 3D scanner. After design in the CAD software, the restoration can be produced by CAM software. Present dental CAD software, however, does not support interaction with the patient, if anything because the present CAD modeling process generally starts from prepared teeth—too late for the patient to influence the treatment to a significant degree. Thus, a main object of the invention is to provide digital design of dental restorations at an earlier stage of the design process.

This is achieved by a method for planning dental restoration on at least a part of the pre-prepared teeth of a patient, wherein said method comprises the steps of:
  providing at least one 3D digital model of at least a part of the pre-prepared teeth;
  designing at least one dental restoration CAD model based on the 3D digital model of at least a part of the pre-prepared teeth;
  providing at least one 3D digital model of at least a part of the prepared teeth, where the prepared teeth are provided by preparing the pre-prepared teeth by dental restorative work, preferably at least partly based on the dental restoration CAD model; and
  aligning the 3D models of the pre-prepared and the prepared teeth.

Thus it is an advantage that the method provides alignment or merging of multiple 3D data sources and exploitation of the results of pre-treatment analysis and planning.

It is an advantage of the method that the dentist can design and show a dental restoration CAD model, which is a virtual model, to the patient, before the dentist starts preparing the patient's teeth, such that the patient can see what the dental restoration will look like. Since the dental restoration CAD model is based on the 3D digital model of patient's pre-prepared teeth, the dental restoration will give a true image of how the dental restoration will really look. Thus the patient has a chance to say if he wishes the dental restoration to have a different shape, size etc. before the dentist starts preparing the patient's tooth/teeth.

Then after the dentist has prepared the patient's teeth to receive or fit to the agreed dental restoration, a 3D digital model of the prepared teeth is provided. There is now a 3D model of the pre-prepared teeth and a 3D model of the prepared teeth, and these two models are then aligned. When aligning the two models it is possible to obtain a dental restoration with a perfect fit because both the pre-prepared teeth and the prepared teeth are used in the design such that the original teeth and the prepared teeth are taken into account.

The pre-prepared teeth can be the patient's teeth before any treatment has been applied. However, the pre-prepared teeth may also be the patient's teeth prior to the preparation work that is often required prior to a dental restoration. Therefore the pre-prepared teeth may have received some (typically minor) treatment, such as cleaning, polishing, minor grinding and/or the like, but the pre-prepared teeth have not been prepared for a dental restoration. A preparation for a dental restoration typically requires grinding, drilling, removal, endodontic treatment and/or the like, of relevant tooth/teeth. All in all: by the present invention a possible dental restoration can be provided by means of CAD with basis in a 3D model of the pre-prepared teeth.

Thus embodiments of the invention relates to planning, visualizing, optimizing and/or executing dental restorative work by means of CAD.

Prior to dental restorative work relevant tooth/teeth are prepared. Thus, the 3D model of the pre-prepared teeth may also be prepared. In a further embodiment of the invention a dental preparation CAD model is designed, preferably at least partly based on the model of the pre-prepared teeth.

Thus, the present invention provides procedures to effectively transfer pre-preparation design work to the actual preparation procedure, and even to the post-preparation design phase. This is illustrated in FIG. 1. And furthermore, duplicate design work for pre-prepared and prepared teeth is avoided.

A related objective is to avoid the manual production of diagnostics wax-ups in relation to planning, evaluation and execution of dental restorations.

The prior art documents related to orthodontics do not disclose designing dental restorations, since orthodontics is related to moving teeth by means of appliances, such as dental braces, headgear etc., and therefore in orthodontics no dental restorations are designed.

Models, such as virtual 3D models, mentioned in relation to orthodontics are models of the configurations or arrangements of teeth in the different steps in an orthodontic treatment and planning, because the teeth will be moved stepwise over longer time by means of the appliances.

The prior art document US 2008/0153061 does for example not disclose the steps of aligning the 3D models of the pre-prepared and the prepared teeth.

In some embodiments the method further comprises transferring the design of the dental restoration CAD model to the model of the prepared teeth. When transferring the design of the dental restoration CAD model to the model of the prepared teeth, the design can be adjusted to fit the model automatically and/or manually.

A further object of the invention is to visualize proposed restorations, possibly along with the patient's face. This is achieved by providing a facial 3D digital model of the patient, preferably with at least a part of the teeth being visible and/or exposed, preferably provided by means of scanning at least a part of the face of the patient, preferably optical scanning.

A further embodiment of the invention comprises the step of at least partly aligning the 3D model of the pre-prepared teeth and/or the dental restoration CAD model with the visible teeth in the facial 3D model.

In a further embodiment of the invention the dental restoration CAD model is at least partly designed based on the facial 3D model.

A further embodiment of the invention comprises the step of providing a preparation guide for the dentist prior to preparing the teeth, said preparation guide preferably at least partly based on the dental preparation CAD model.

In a further embodiment of the invention said preparation guide provides assistance in relation to lengthening of crown(s), location and/or type of the margin, and/or the like, and wherein the generation of said preparation guide is at least partly based on the dental restoration CAD model and/or the 3D model of the pre-prepared teeth and/or the dental preparation CAD model and/or segmentation of said models.

In a further embodiment of the invention said preparation guide comprises instructions for execution of a machine generated preparation and/or preparation model.

In a further embodiment of the invention said preparation guide comprises a dental model of the preparation, such as a gypsum model and/or a wax-up model, such as a marked-up dental model.

A further embodiment of the invention comprises the step of transferring the design of the dental restoration CAD model comprises aligning the dental preparation CAD model with the 3D model of the prepared teeth.

In a further embodiment of the invention aligning is at least partly based on detecting and/or demarcating and/or aligning margin lines of the models.

In a further embodiment of the invention transferring the design of the dental restoration CAD model comprises morphing part of the dental restoration CAD model to the 3D model of the prepared teeth.

In a further embodiment of the invention morphing is applied near the margin line of the dental restoration CAD model and/or the 3D model of the prepared teeth.

In a further embodiment the impact of morphing is highest near the margin line of the dental restoration CAD model and/or the 3D model of the prepared teeth, with decreasing impact of the morphing when increasing the distance to the margin line.

A further embodiment of the invention, the step of transferring the design of the dental restoration CAD model comprises creating an inner surface of the dental restoration CAD model as an offset to the 3D model of the prepared teeth, said offset preferably in the occlusal/incisal direction from the margin line of the 3D model of the prepared teeth.

In a further embodiment of the invention said offset is provided automatically.

In a further embodiment of the invention a significant part of the outer surface of the dental restoration CAD model is maintained when transferred to the 3D model of the prepared teeth, the contour of the inner surface of the dental restoration CAD model is substantially similar to the outer surface of the 3D model of the prepared teeth and the margin line area of the dental restoration CAD model and the 3D model of the prepared teeth are morphed together.

Yet a further embodiment of the invention comprises the step of transferring the design of the dental restoration CAD model comprises morphing the dental preparation CAD model with the 3D model of the prepared teeth, thereby providing a transformation of the dental preparation CAD model to the 3D model of the prepared teeth, and subsequently applying this transformation to the dental restoration CAD model.

A further embodiment of the invention comprises the step of modifying the design of the dental restoration CAD model subsequent to the step of transferring said dental restoration CAD model to the 3D model of the prepared teeth.

Yet another embodiment of the invention relates to a method for planning, visualizing, and/or optimizing dental restorative work on at least a part of the teeth of a patient, said method comprising the steps of:

providing a 3D digital model of at least a part of the face of the patient, preferably with at least a part of the patient's teeth being visible and/or exposed, preferably provided by means of optically scanning at least a part of the face of the patient, obtaining at least one 3D digital model of at least a part of the prepared teeth, where the prepared teeth are prepared by dental restorative work, aligning the 3D model of the prepared teeth with the visible teeth in the 3D facial model, and designing at least one dental restoration CAD model based on the 3D model of the prepared teeth and at least partly based on the 3D facial model.

In a further embodiment of the invention the 3D model of the pre-prepared and/or the 3D model of the prepared teeth are provided by means of scanning, such as scanning intra orally, scanning an impression of the teeth and/or the antagonist, scanning a cast of the teeth and/or the antagonist, and/or the like scanning methods.

Yet a further embodiment of the invention comprises the step of calculating margin lines of the 3D models.

In a further embodiment of the invention the 3D facial model face, the 3D model of the pre-prepared teeth and/or 3D model of the prepared teeth and/or the dental restoration CAD model and/or the dental preparation CAD model comprises information of geometry and/or texture (color).

In a further embodiment of the invention color is detected by means of at least one color sensitive sensor and/or by means of stacking of color channels.

In a further embodiment of the invention the 3D facial model is provided by means of aligning and/or combining multiple sub-scans of the face, preferably sub-scans provided from different angles.

In a further embodiment of the invention at least part of the sub-scans are at least partially overlapping.

In a further embodiment of the invention at least a part of the sub-textures of at least a part of the sub-scans are color adjusted and/or color interpolated, such as by texture weaving, to provide the texture of the 3D facial model.

In a further embodiment of the invention at least part of the hair of the patient is powdered with a reflective powder.

In a further embodiment of the invention silhouettes from multiple sub-scans are extruded and subsequently intersected to provide a visual hull approximation.

Yet a further embodiment of the invention comprises the step of cutting and/or removing at least a part of the teeth from the 3D facial model.

In a further embodiment of the invention design of the dental restoration CAD model is at least partly based on biometric information for optimizing the aesthetic impression of the dental restoration, biometric information such as degree of maxillary anterior tooth display (Morley ratio), upper lip drape and gingival display.

In a further embodiment of the invention wherein the facial midline is substantially aligned with the arch midline, and/or the incisal plane and the interpupillary line are provided substantially parallel.

In some embodiments of the invention the face scanner is used to measure features of the face of the patient, such as the facial midline, the arch midline, the incisal plane, and/or the interpupillary line.

Yet a further embodiment of the invention comprises the step of providing a least one X-ray image of at least a part of the head, the jaw, the pre-prepared and/or the prepared teeth.

In a further embodiment of the invention multiple X-ray images obtained from different angles are combined to provide a 3D X-ray model.

In a further embodiment of the invention the 3D X-ray model is aligned with and/or visualized along one or more of the 3D models and/or the CAD models.

In a further embodiment of the invention automatic and/or semi-automatic assistance is provided in the design of the dental restoration CAD model and/or the dental preparation CAD model, assistance such as automatic suggestions, evaluation of basic rules and requirements and/or the like, requirements such as medical and/or biologic requirements.

In a further embodiment of the invention a library of standard restorations and/or standard preparations is provided when designing the dental restoration CAD model and/or the dental preparation CAD model, a library such as a library of CAD models.

Yet a further embodiment of the invention comprises the step of estimating the strength of a planned dental restoration, such as estimating by means of finite-element simulation.

A further embodiment of the invention comprises the step of visualizing the dental restoration CAD model, for example for the patient, dentist and/or dental technician.

In a further embodiment of the invention the dental restoration CAD model is visualized side-by-side, along and/or on top of the model of the pre-prepared teeth.

A further embodiment of the invention comprises the step of visualizing the dental restoration CAD model aligned in the facial model.

A further embodiment of the invention comprises the step of predicting and/or visualizing the facial soft-tissue-change occurring as a result of the dental restorative work.

In a further embodiment of the invention visualization is provided in 3D, such as visualization of 3D models and CAD models.

In a further embodiment of the invention visualization is provided by means of at least one computer screen and/or by means of manufacturing of at least one diagnostic wax-up. Thus, the 3D models and/or the CAD models can be presented on a computer screen, however the models may also be physically realized e.g. by 3D printing in gypsum or wax.

In a further embodiment of the invention visualization is provided over a computer network, such as the internet.

Yet a further embodiment of the invention comprises the step of predicting and/or visualizing the facial soft-tissue-change occurring as a result of the dental restorative work.

Yet a further embodiment of the invention comprises the step of at least partially segmenting teeth and tissue, such as gingival, in the 3D model of the pre-prepared teeth and/or in the 3D model of the prepared teeth and/or in the 3D facial model.

In a further embodiment of the invention segmentation is at least partly provided by means of a computer implemented algorithm, such as a shortest-path algorithm applied on a 3D matrix representing curvature of the tooth surface.

In a further embodiment of the invention segmentation is at least partly based on color information in the 3D model(s).

A further aspect of the invention relates to a method for planning, visualizing, and/or optimizing dental restoration on at least a part of the pre-prepared teeth of a patient, where said method comprises the steps of:
    providing at least one 3D digital model of at least a part of the pre-prepared teeth;
    designing at least one dental restoration CAD model based on the 3D digital model of at least a part of the pre-prepared teeth;
where the method further comprises the step of:
    simulating and estimating dynamic occlusal interferences, and wherein said interferences are deduced at least partly from a plurality of scans that record said patient's jaw articulation by tracking at least one reference object fixed to the patient's teeth Yet a further embodiment of the invention comprises the step of calculating the articulation of the jaw and thereby simulating and/or estimating dynamic occlusal interferences.

In some embodiments of the invention the face scanner is used to measure 3D movements of the jaws and face of the patient in real time.

In some embodiments of the invention the face scanner is used to measure the position of the upper jaw and/or lower jaw with respect to the skull. Thus the face scanner may then replace a face-bow, which is traditionally used for this measurement.

Thus the face scanner can be used to measure planes of the face, such as centric determination or the midline, it can be used to measure jaw movement, and/or it can be used to measure the attachment and/or movement of the jaws relative to the rest of the skull.

Thus the measured jaw motions, which are the physically true motions or movements, are used to simulate the movement in a dynamic virtual articulator, such that dental restorations can be designed, where the dental restorations have improved functionality and aesthetics. Thus the face scanner can perform the relevant measurements for providing a dental restoration, and thereby replacing the use of e.g. face-bows etc.

In a further embodiment of the invention calculation and/or estimation of the articulation of the jaw and/or the dynamic occlusal interferences is at least partly based on a plurality of face scans and at least one 3D model of the pre-prepared and/or prepared teeth, a 3D model that comprises the antagonist. For optimal accuracy and precision, it is advantageous to fix one or more reference spheres or objects to the teeth.

Yet a further embodiment of the invention comprises the step of interactively modifying and/or optimizing the design of the dental restoration CAD model, preferably based on input from a dentist and/or the patient and/or from considerations relating to aesthetic appearance, biometrics, medial and/or biological rules and/or requirements, estimation of strength, soft-tissue change, occlusal interferences, color issues, cost of restoration and/or the like.

Design and/or design modifications of the dental restoration CAD model can be provided by a dentist and/or dental technician in cooperation with the patient. However, with digital models the involved patients do not have to be at the same location because the models can be distributed, presented and/or visualized via a computer network. Thus, in a further embodiment of the invention wherein interactive modification and optimization of the dental restoration CAD model is provided across a computer network, such as patient, dentist and/or dental technician being located at different geographic locations. E.g. the patient may be at home while the dentist is presenting the dental restoration CAD model, such as via a web page. Or the dentist and the patient may be at a dental clinic, together evaluating a dental restoration model for the patient provided by a dental technician at a dental lab in another location.

A further embodiment of the invention comprises the step of evaluating and/or validating a preparation guide and/or a set of prepared teeth, preferably at least partly based on a 3D model of said prepared teeth.

In a further embodiment of the invention evaluation and/or validation comprises estimating and/or evaluating a proposed dental restoration, choice of materials, choice of restorative method, and/or the like.

In a further embodiment of the invention a dental restoration can be one or more inlays, onlays, veneers, crowns, bridges or combinations thereof and/or a dental restoration can be a removable partial denture framework and/or an implant-retained structure.

In another embodiment of the invention planning, visualizing, optimizing and/or executing dental restorative work is combined with planning, visualizing, optimizing and/or executing of plastic surgery applied to the head and/or face.

In a further embodiment the method further comprising planning, visualization, and/or optimization of at least one "snap on", wherein a "snap-on" CAD model is created by subtracting the 3D model of the pre-prepared teeth from the dental restoration CAD model.

Yet a further embodiment of the invention comprises the step of manufacturing of a dental restoration for the prepared teeth based on the dental restoration CAD model, preferably by means of CAM.

A further embodiment of the invention comprises the step of manufacturing of a diagnostic wax-up based on the dental restoration CAD model, preferably by means of CAM.

A further embodiment of the invention comprises the step of manufacturing of a preparation guide for the prepared teeth based on the dental preparation CAD model, preferably by means of CAM.

A further embodiment of the invention comprises the step of manufacturing of a diagnostic wax-up based on the dental preparation CAD model and/or the preparation guide, preferably by means of CAM.

In a further embodiment of the invention CAM instructions for manufacturing of the dental restoration are provided and/or distributed by means of a computer network, such as transferred to a processing centre via the internet.

In a further embodiment of the invention any listed step at least partly is provided by means of CAD or can be provided by means of CAD.

In a further embodiment the method further comprises designing a temporary crown, where the temporary crown is derived from the CAD design.

A further embodiment of the invention relates to design and/or manufacture of snap-ons.

The entire process of deciding upon—preferably interactively with the patient—and then designing a dental restoration is now fully digitally supported.

The invention furthermore relates to a system comprising means for carrying out any of the listed methods.

The invention furthermore relates to a computer program product having a computer readable medium, said computer program product comprising means for carrying out any of the listed methods.

A preferred embodiment of this invention allows for interactive design of restorative treatment, thus increasing the chance for complete patient satisfaction. In terms of interactivity this invention is based on 3D models, contrary to for example U.S. Pat. No. 6,786,726 that only relates to 2D digital images.

One embodiment of the invention provides a method and a system to plan and execute dental restorative treatment mainly relying on 3D data and without the need for a physical diagnostic wax-up. Preferably, also color 3D scans of the patient's head are obtained and used within the planning process, making it even more comprehensive and realistic. Methods described this application can be interactive between the patient and the dentist, thus ascertaining the patient's accept of the proposed treatment. As another advantage, the 3D data obtained in the pre-treatment phase can be exploited when the restoration is actually designed for manufacture by CAM.

In one embodiment, the invention concerns a system and method for planning dental restorative treatment and designing a dental restoration based on a 3D digital model of the patient's teeth in the pre-preparation state, where this planning and design is implemented in software only. Thereby, the system and method has the advantages of a diagnostic wax-up without its disadvantages of high costs and tedious and time-consuming manufacture.

The dentist can even design the restoration interactively with the patient. Once a design has been decided on, the dentist will generally prepare the teeth accordingly, and generate another 3D model of the prepared teeth. The final design will be based on the prepared state, but can exploit the pre-preparation design.

Optionally in said embodiment, the invention includes a system and a method to obtain a colored 3D model of the patient's head. This latter model is usually obtained with another type of scanner, and it need not have the same high level of detail as the 3D model of the teeth. To visualize the effects of treatment, the teeth in the head model are replaced by the CAD-designed teeth (i.e., the teeth as they would appear post-treatment), using some kind of alignment technique and information from the 3D model of the teeth prior to CAD design. The result is a composite 3D model of head and teeth that can visualize the effect of potential restorative work even better than a 3D model of teeth alone.

In another embodiment of the invention, the colored 3D model of the patient's head is required, whereas the digital model of teeth in their pre-preparation state is not. The design of the restoration after a model of the prepared teeth is obtained can take advantage of the information in the face model in the same way as the previous embodiment.

The present invention relates to different aspects including the method described above and in the following, and corresponding methods, systems, devices, uses, and/or product means, each yielding one or more of the benefits and advantages described in connection with the first mentioned aspect, and each having one or more embodiments corresponding to the embodiments described in connection with the first mentioned aspect and/or disclosed in the appended claims.

In particular, disclosed is a system for planning, visualizing, and/or optimizing dental restoration on at least a part of the pre-prepared teeth of a patient, wherein said system comprises:
  means for providing at least one 3D digital model of at least a part of the pre-prepared teeth;
  means for designing at least one dental restoration CAD model based on the 3D digital model of at least a part of the pre-prepared teeth;
  means for providing at least one 3D digital model of at least a part of the prepared teeth, where the prepared teeth are provided by preparing the pre-prepared teeth by dental restorative work, at least partly based on the dental restoration CAD model; and
  means for aligning the 3D models of the pre-prepared and the prepared teeth.

Definitions

A 3D model (aka a 3D digital model) can be either point clouds, surface (faceted/meshed), or volumetric. Faceted/meshed models are preferred over point clouds, but faceted/meshed models can be generated from point clouds, for example by triangulation. Volumetric models can be obtained with a scanner applying penetrating radiation, such as CT scanners.

A restoration CAD model is a virtual computer model of a restoration. Similarly: a preparation CAD model is a virtual computer model of a preparation. CAD models are created in a software program and can be based on one or more 3D models of the patient teeth. Thus, whereas a 3D model is typically a digital representation of a physical object, a CAD model is a virtual digital model, however possibly at least partly comprising a digital representation of at least a part of a physical object.

A restoration is a classical fixed restoration such as inlays/onlays, veneers, crowns, bridges, implant-retained structures etc, but by analogy also removable restorations such as dentures. A restoration requires dental restorative work.

A preparation guide is a recommended procedure to execute a dental preparation. It may be in the form of documents, audiovisual material, or physical artifacts such as example dental models. It may contain information concerning which equipment to use and how to use it. Thus a preparation guide is typically directed at a dentist, a dental technician, a dental lab and/or the like. A preparation guide may comprise (software) instructions that can be executed by a machine used for the preparation.

A patient is the person for whom a restoration is designed. There may be medical indications for dental treatment of this patient, but also cosmetic considerations can be a relevant motivation for having a dental restoration designed.

DESCRIPTION OF DRAWINGS

The above and/or additional objects, features and advantages of the present invention, will be further elucidated by the following illustrative and non-limiting detailed description of embodiments of the present invention, with reference to the appended drawings, wherein:

FIG. 6: Graphical representation of some steps in this invention.

DETAILED DESCRIPTION

In the following description, reference is made to the accompanying figures, which show by way of illustration how the invention may be practiced.

Figure 1:
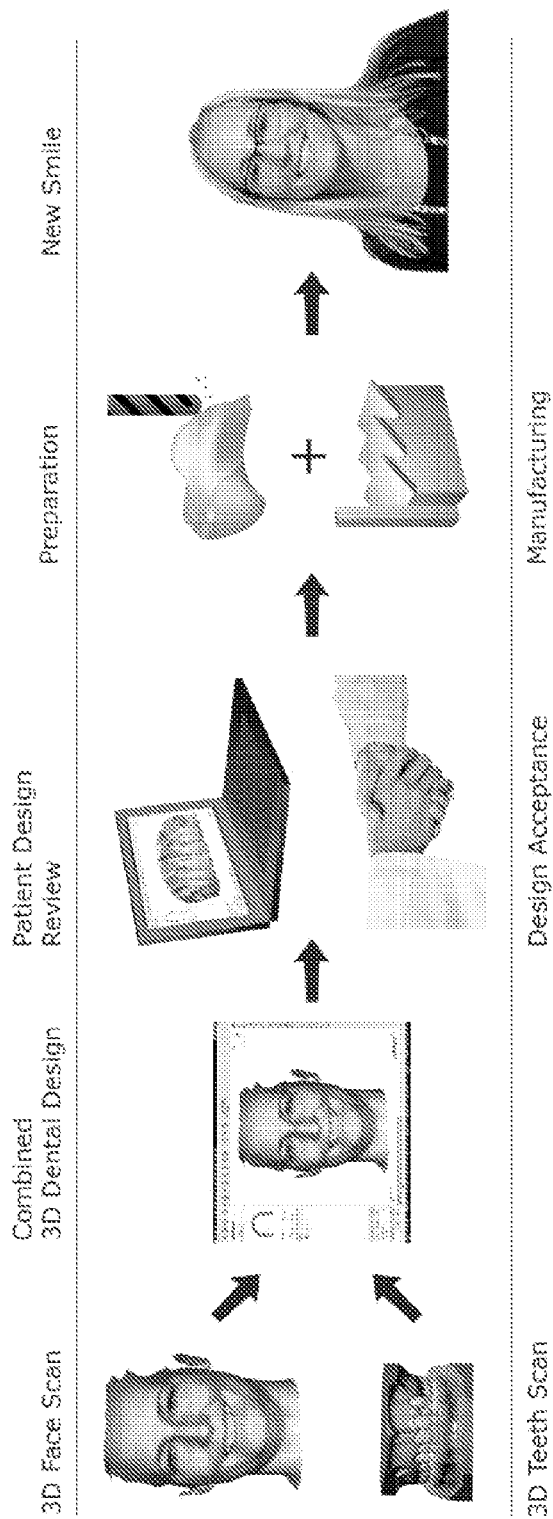
FIG. 1: Motivation for this invention, outline of flowchart with graphical illustrations for clarity.
Figure 2:
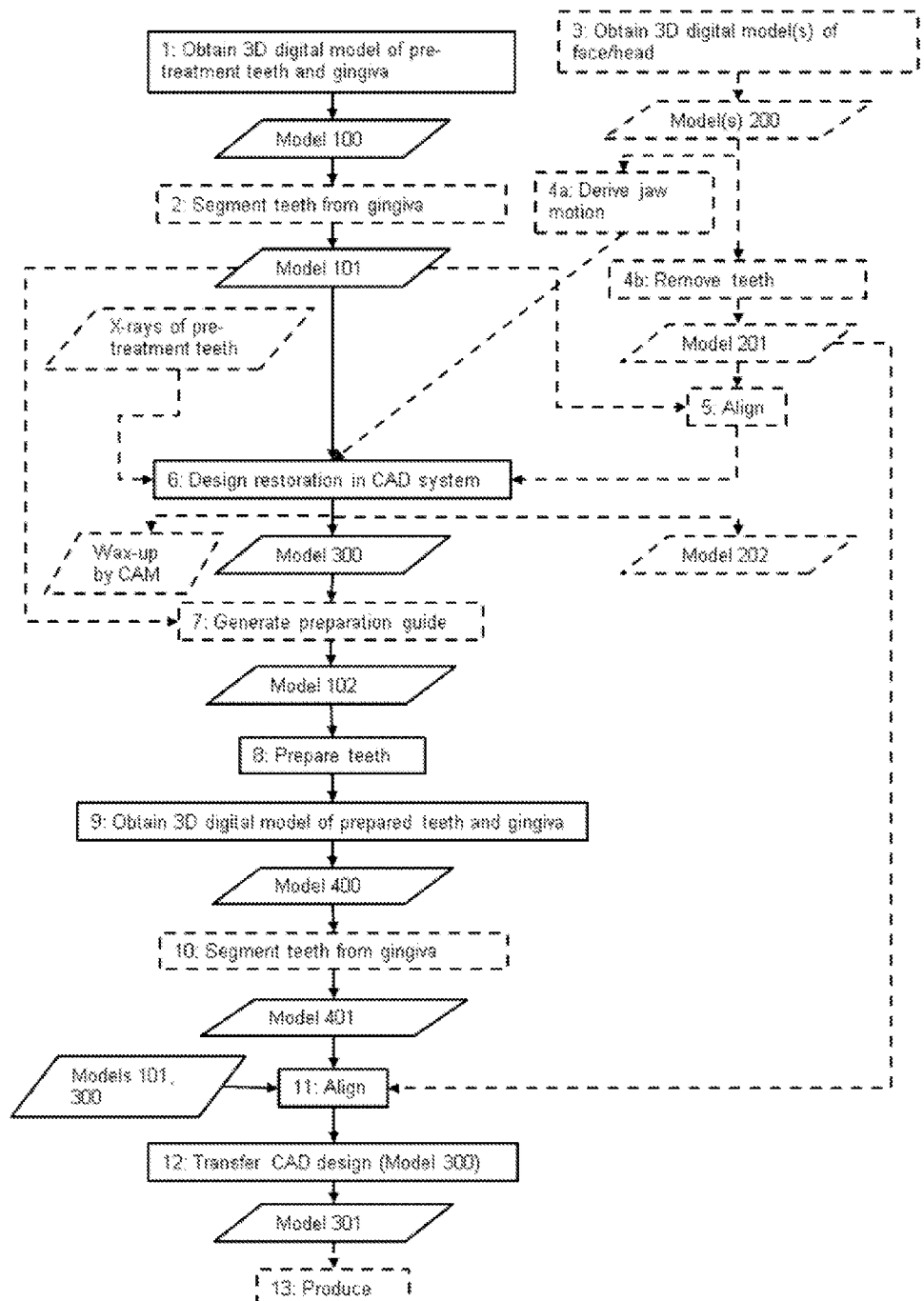
FIG. 2: Detailed flow chart for variant V1 of the method described in this invention.

In one embodiment of the invention (in the following termed "V1" and illustrated in the flow chart in FIG. 2) a pre-treatment (pre-prepared) 3D model of the patient's teeth is used, preferably obtained with a 3D scanner. Optionally, another 3D model of the patient's face (possibly obtained with another type of scanner) is exploited for optimal alignment and/or aesthetic look of the restoration.

Figure 3:
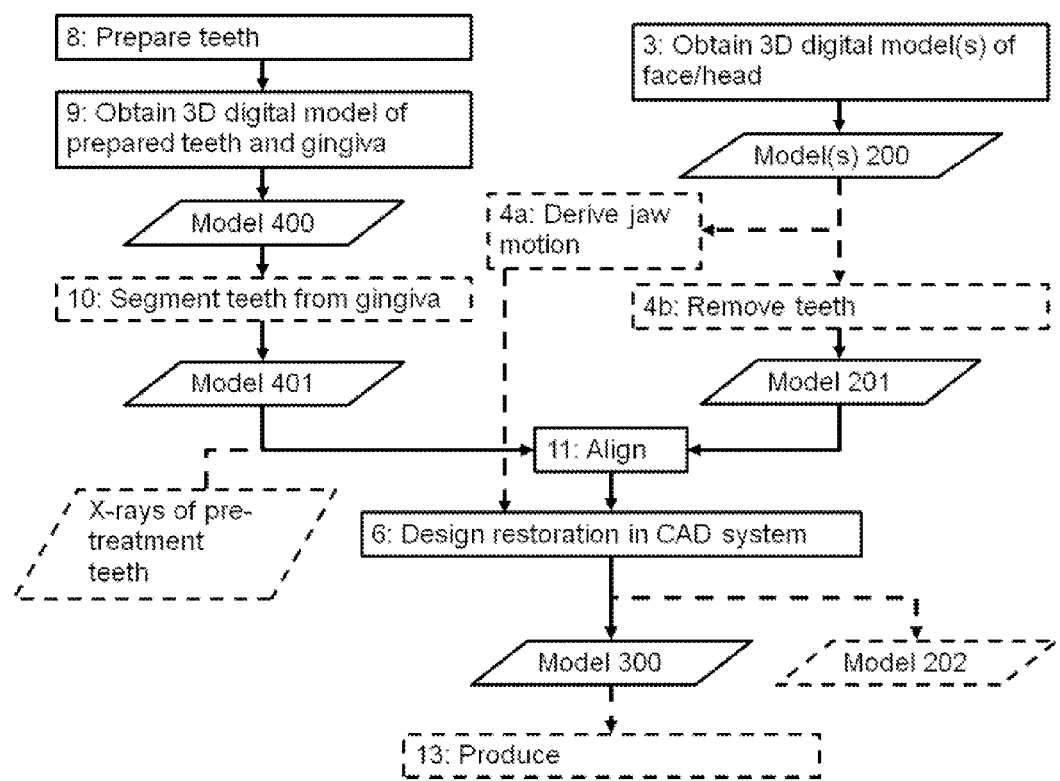
FIG. 3: Detailed flow chart for variant V2 of the method described in this invention.

In another embodiment of the invention (in the following termed "V2" and illustrated in the flow chart in FIG. 3), the 3D facial model is required, while the pre-treatment 3D model is optional.

Both V1 and V2 may comprise similar steps, however in a different combination and with slight differences. Optional steps and models in V1 and V2 are indicated by dashed borders in the flowchart elements. Some steps are optional only in V1 or V2.

Some steps may be implemented in software, while others may represent manual work and/or application of machinery. The software is preferentially a single program, for optimal ease of use.

Some steps are also illustrated graphically in FIGS. 4-7.

Figure 4:
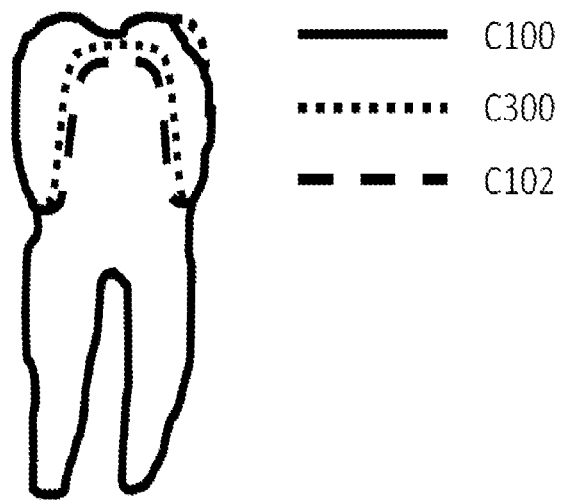
FIG. 4: Sagital section of a schematic tooth, visualizing various steps of the method described in this invention.

Step 1: Obtain 3D Digital Model of Pre-Treatment Teeth and Gingiva (Required in V1, not Applicable in V2):

There are several commercial systems available for obtaining 3D digital models 100 of teeth (e.g., Cadent iTero, 3M ESPE Lava, 3Shape D640). Among these are intra-oral scanners and scanners for dental impressions or casts thereof (e.g., 3Shape D640). Scanners can be for example be optical scanners (laser, structured light). Guidelines in the relevant scanner manufacturer's operations manual should be followed for obtaining the 3D model 100. This model 100 will in the following also be denoted as the pre-preparation model. Its contour in FIG. 4 is C100.

Potentially, scanners with penetrating radiation such as (cone beam) CT scanners (Imaging Science International's i-CAT, Kodak/Imtec's Iluma) can be used to obtain model 100. They have the advantage of providing volumetric models showing also decay inside the teeth, while disadvantages include concerns about radiation dose or high price of treatment. A teeth scan is shown in FIG. 6, step 1.

Step 2: Segment Pre-Prepared Teeth from Gingiva (Optional in V1, not Applicable in V2):

Optical scanners generally obtain a 3D digital model of an object's surface. While this model describes geometry, it does not differentiate between any materials or sub-objects that make up the surface. Specifically for dental applications, the 3D model does not differentiate between teeth and gingival, some of which inadvertently will be included in a teeth scan. For visualization and CAD design of dental restorations, it can therefore be advantageous to segment the combined 3D model into teeth and tissue, respectively. Segmentation can be applied by means of an algorithm implemented in software, yielding model 101. A segmented teeth model is shown in FIG. 6.

In one embodiment of the invention, the segmentation algorithm uses vectors perpendicular to each tooth, or a single vector, perpendicular to the whole model, and one point in the middle of each tooth or two points on the distal and mesial sides of the tooth. A preferred version of the separation algorithm is based on using a 3D shortest path algorithm, preferably capable of handling negative weights, for example the Bellman-Ford algorithm. The algorithm is preferably applied on a 3D matrix with elements representing curvature of the surface of the tooth model 100.

In another embodiment, the scanner used to generate model 100 can capture color as well. Segmentation can then be based on color information.

If step 2 is skipped, models 100 and 101 are identical.

Step 3: Obtain 3D Digital Model(s) of Face/Head (Optional in V1, Required in V2):

There are several systems available for obtaining 3D digital models of the head, particularly the face (e.g., Konica Minolta Vivid, Breuckmann faceScan). Head/face and dental scanners are generally different instruments, because the required resolution for head/face scans is generally lower, while the volume of interest is larger. Most optical head/face scanners employ structured light.

In a preferred embodiment of this invention, the head/face scanner can detect not just surface geometry, but also color. Color (also termed texture) information is important in visualization. Color can be detected directly by choosing a color-sensitive sensor in the scanner's camera(s). Another approach is to use a sensor sensitive to total light intensity only, but take several images where the illumination is a single base color in each, and then reconstruct the color by combining those images. This process is also called stacking of color channels, and typical base colors are red, green, and blue.

It is preferable to scan the head/face with the patient exposing his or her teeth. This constellation can be exploited in step 6. Generally, the patient will want to smile, because the aesthetic appearance of a dental restoration is often viewed most critical for a smile.

A 3D model of the head may require several scans from different angles. Multiple such scans have to be aligned to a combined model. Many algorithms exist for this purpose, for example Iterative Closest Point. They all require some overlap of at least pairs of sub-scans. As lighting in every sub-scan generally will differ, the sub-textures need to be color-adjusted for the combined texture. For example, texture weaving can be employed to smooth color differences between different sub-scans [4].

Due to limited reflectivity, the hair portion of the head is generally difficult to capture with optical scanners. This limitation can be overcome by powdering the hair with a reflective powder. Another method to reconstruct the hair portion in 3D is to extrude the silhouettes in multiple head images (taken from different angles) and then to intersect them to form the visual hull approximation.

Subsequent to step 3, the flow charts splits into two branches. These branches are not alternatives, but can both be executed. They start with steps 4a and 4b, respectively.

Step 4a: Derive Jaw Motion (Optional in V1, Optional in V2):

Especially for crown design, it can be advantageous to account for dynamic occlusal interferences. With a plurality of face scan models 200, it is possible to deduct the articulation of the jaw and thus simulate dynamic occlusal interferences given a 3D model of the teeth 101 that includes the antagonist. To deduct the articulation from 3D facial models, it may be advantageous to fix one or more reference sphere(s) to the patient's mandibular teeth, preferably between the lower lip and the mandibular incisors, and to track that sphere's motion. The procedure is described for a single sphere and 2D images in [9], but can be expected to be more precise with 3D data, and to correctly detect rotational movements if more than one sphere is used. Additional sphere(s) or object(s) can also be fixed on the patient's maxillary teeth. With 3D data, any concurrent movement of the head can be separated from movement of the jaw during chewing. WO 2009/091439 discloses a procedure where 3D movements are deducted by tracking dental objects. This is however much less accurate than using reference sphere(s), because spheres, unlike dental objects, have a perfect geometric surface from which it is possible to determine a center position with high precision and accuracy. Accordingly, many metrological standards employ reference spheres, e.g. ISO 10360-3.

Step 4b: Remove Teeth (Optional in V1, Optional in V2):

If any face/head model 200 shows the teeth (and possibly the gingival scaffold), it can be advantageous to cut them out, and to later (e.g. in step 6) display the teeth/gingiva model 101 (V1) or 401 (V2) in their place. The latter model will often have a higher degree of detail, as a high level of detail is required for modeling the dental restoration in step 6. The cutting could also apply to only some of the teeth, for example if the model 101 or 401, resp., only has some teeth, or even a single tooth. Said cutting is performed in software, where it can be performed interactively or at least partially automated.

Interactive cutting can for example be performed in 3D software by placing a 3D line on the model, cutting out all points and/or facets inside the line. Possibly, facets can be sub-divided along the cutting line, such that the cutting line is respected precisely. One way of entering the cutting line in the 3D software is to click on some reference points, and use a spline to connect them. The spline should follow the surface of model 200.

Automated cutting can be performed by detecting teeth (and possibly gingiva) by software algorithms. For example, teeth can be detected as such by their color and/or their shape.

If model 101 or 401, resp., includes a complete set of teeth, the inner commissure is the preferred section in model 200 to cut out, as delineated by the innermost confluences of the vermillion of the lips at the corners of the mouth [1].

Step 5: Align Teeth Model to Face Scan (Optional in V1, not Applicable in V2):

In this step, the teeth/gingiva model 101 is aligned with some head/face model 200, or—if step 4 was performed—the cut head face model 201. In other words, the position of model 101 becomes that of the corresponding portion of model 200/201, and both can be displayed simultaneously in a meaningful way. Alignment is thus a rigid transformation of at least one model, either into the local coordinate system of the other, or into some other common coordinate system.

The alignment is preferably performed in software, interactively and/or automatically. Interactive alignment can be performed in the graphical user interface provided by the software by dragging a model (translation), or dragging some control points for rotations. Another way to transform a model is to enter or adjust the transformation matrix directly.

The criterion for alignment can be a subjective visual fit or be defined mathematically. A common such criterion is the sum of squared distances between the two models. Distances are usually measured in the direction of the surface normals. Other criteria could be based on the distances between certain features, such as the incisal planes, or the midline(s) between incisors.

Automatic alignment can be performed using the same algorithms as in step 3. Possibly, the user will have to place control points for corresponding points of the models to be aligned, those serving as a first guess for the automated fine alignment. Automated alignment is an optimization of the mathematically defined fit criterion. In case the head/face model 200 does not expose the teeth on the surface, alignment with the teeth/gingiva model 101, alignment can still be possible if the head/face model is a cephalogram (x-rays of the head) [5].

Step 6: Design Restoration in Cad System (Required in V1, Required in V2):

This step is largely identical in both variants (i.e. V1 and V2), but starts from the pre-prepared teeth in variant V1, while in variant V2, it starts from the prepared teeth. The earlier position in the work flow in variant V1 allows some additional possibilities in this variant.

Common Features in Step 6 in Both Variants V1 and V2:

Dental restorations that can be designed in a CAD system include inlays, onlays, veneers, crowns, bridges, combinations thereof, and others. By analogy, the term "restoration" also covers removable partial denture frameworks and implant-retained structures. Several dental CAD software packages that allow such design are available, for example 3Shape DentalDesigner. Model 300 is that of the restoration only. In this step 6, it is only a digital model. Its contour in FIG. 4 is C300. The restoration implies requirements for the preparation. As model 300 is digital, the preparation is also virtual in this step 6. For a given restoration model 300, there can be many possible virtual preparations C102, however some may be more advisable than others (see step 7). An example contour of a virtual preparation in FIG. 4 is C102. Mainly, C102 is offset from C300 by the cement space. Note that the thickness of the cement space in FIG. 4 is exaggerated for graphical clarity only.

The software used in this step 6 should preferably assist the dentist/dental technician in designing the restoration, for example by making automatic suggestions and/or evaluating basic rules and requirement.

Basic rules and requirements, preferably implemented in the software, may include the minimum thickness for the restoration (generally dependent on material) and biologic width. Other rules could ascertain the mandatory continuous circumferential height of a preparation for a crown. The strength of a restoration could be determined numerically, for example by measuring the thickness or preferably a finite-element simulation. Yet another rule could be to not to penetrate the antagonist and proximal teeth.

In the common case of the head model 101 not being a volumetric one, it can be advantageous to integrate x-ray images in this step 6, because the extent of decay visible in these will constrain the choice of restoration. If multiple x-ray images are taken from different angles, it will be possible to create an approximate 3D model from the silhouettes in all images, analogously to how the hair can be reconstructed in 3D in step 3. The resolution in 3D of this model will however generally be poor, because only few X-rays can be taken. Because of this poor quality, said integration of x-ray images in step 6 may not be a proper alignment to the other models, but at least a concurrent visualization in the software. Possibly, the software can detect the image planes of the x-rays in the 3D model of the teeth (101 in variant V1, 401 in variant V2) by a best fit between their sections, and then automatically set the view port in the 3D visualization of the latter models to match the image planes of the x-rays.

A major advantage of this invention is that it enables a dialog between the patient and the dentist regarding the treatment, optionally involving the lab also. For example, the dentist can visualize the proposed restoration on a computer screen. Preferably, the CAD software that the dental technician/dentist uses for the virtual design of the restoration itself provides such visualization and can be used interactively to update the design in dialog with the patient. The technician/dentist could propose visual appearance and aesthetic as well as explain functional advantages and disadvantages of potential restorations, along with cost. A physical diagnostic wax-up could also be manufactured by CAM, still more cheaply and quickly than traditional diagnostic wax-ups.

It is advantageous to be able to render the available 3D models photo-realistically. Graphics functionality on PCs, like OpenGL, aids towards this goal. Proper, or even adjustable, coloring of gingiva and teeth, respectively, or regions thereof, in teeth/gingival models (101 in variant V1, 401 in variant V2) is likewise advantageous. Even if said models were obtained with a color-enabled scanner, the lighting used to capture it is generally different from that applied when capturing model 200, leading to a visual mismatch in the display of all models aligned (step 5). Special computer graphical techniques, like ray tracing, can improve the visual appearance, along with the modeling of more than one light source.

When a face/head model 201 is available, biometric information can be exploited for optimizing the aesthetic impression of the dental restoration [6]. For example, it often appears ideal to align the facial midline with the arch midline, or to achieve parallelism between the incisal plane and the interpupillary line. Metrics for of smile anatomy include the degree of maxillary anterior tooth display (Morley ratio), upper lip drape, and gingival display [1].

If the dental restoration deviates significantly from the existing conditions, it may have effect on the soft tissue near the mouth. 3D facial soft-tissue-change prediction after simulated orthognathic surgical planning has been presented in the literature [e.g., 7], and an analogous procedure could be applied in the context of this invention. The outcome of any (optional) soft-tissue change simulation could be visualized as model 202.

If step 4a has been performed and a trajectory of the mandibular teeth has been determined, dynamic occlusal interferences can be tested in the present invention, allowing the dentist/dental technician to modify model 300 in order to avoid such interferences. This procedure may be at least partially automated removing any parts of model 300 that collide with the antagonist given said trajectory.

When the CAD design is finished, a physical diagnostic wax-up model of the digital model 300, or parts thereof, can be manufactured by CAM. Such manufacturing requires essentially no manual labor and is much less expensive than traditional manual production. The physical wax-up gives the dentist and/or patient another opportunity of evaluating the proposed treatment before it is executed. This may be a relevant procedure especially when the restoration design is performed in a dental lab at another location or the dentist is very traditional. If a physical diagnostic wax-up is created, the lab technician may be required to grind on the pre-preparation model before scanning. In case no physical model exists one can be manufactured by CAM.

In another embodiment of the invention the CAD design can used to create "snap on"s, which can mounted directly on the patient teeth visualizing the treatment result. The "snap on"s are directly created by subtracting the pre-prepared teeth from the design. I.e. the 3D model of the pre-prepared teeth is subtracted from the CAD model of the designed "snap-on" The resulting subtracted design provides the a model of the snap-on's that subsequently can be manufactured by CAM whereupon the snap-on's are ready-to-use.

Communication networks provide other means of establishing interactivity with patient and/or dentist in a situation where the restoration design is performed in another location. For example, the patient and/or dentist could follow the design process via a life internet connection to the designer's computer.

Variant V1 Only:

In one embodiment of this invention, the dentist or dental technician demarcates the desired margin for the restorative design on the teeth model 101 in the software. In another embodiment, the dentist chooses a desired surface of the restoration, e.g., from a crown library (potentially but not necessarily the same as in the corresponding parts in model 101), and the software calculates a margin line. Any combination of said embodiments is also possible, particularly for bridges. Possible automatic suggestions in the software include margin placement, particularly apical placement dependent on tooth number. The dentist may also be offered a selection among a library of standard restorations, which then can be modified.

In this step 6, but also with relevance for the preparation (step 7 below), also temporary crowns can be designed. The temporary crown will be directly derived from the full CAD design in step 6, but with additional cement space e.g. 0.2 mm between the virtual preparation and the inside of the temporary crown. The increased cement space is created to accommodate for inaccuracies in the actual preparation performed by the dentist.

Step 7: Generate Preparation Guide (Optional in V1, not Applicable in V2):

In a preferred embodiment of the invention the software assists the dentist with the preparative work. In many cases, general preparation guides are provided by manufacturers of dental material and equipment. To ease the dentist's work and to improve the restorative strength and overall quality, the invention may provide the preparation guides automatically for the particular design obtained at the end of step 6.

Possibly, the software can assist with planning crown lengthening. In this context, step 2 can be beneficial, preventing the margin from being placed too sub-gingivally. Also the type of margin (bevel, shoulder) could be suggested by the software.

Besides proposing details of the preparation, the software that generates a preparation guide can possibly also validate a preparation that the dentist and/or dental technician have devised by other means. For example, the software can evaluate restorative strength and/or choice of materials, and/or even the choice of restorative treatment method.

The preparation guide can take many forms including instruction text, multiple 2D screen shoots, 3D animations, computer visualization, videos and/or instructions for machined/robot preparation. A preparation guide may also include a physical model of the desired, positive, preparation, or a physical negative representation which can be tested in the mouth of the patient. For example in the case where model 100 is a scanned cast model, the dental technician could prepare this cast. Because the virtual preparation is also available in digital form (the dental preparation CAD model, contour C102 in FIG. 4), it could also be manufactured by CAM.

Step 8: Prepare Teeth (Required in V1, Required in V2):

Based on the agreed restorative treatment and with or without any guide from step 7, the dentist prepares the patient's teeth. The preparation is typically performed by the dentist grinding down the teeth such that the restorative work can be glued on. In variant V1, the preparation will be for the restoration designed in step 6, whereas in variant V2, no prior design determines the preparation work.

Snap-ons (a commercial product by Snap-on Smile) require no invasive preparation.

Step 9: Obtain 3D Digital Model of Prepared Teeth and Gingiva (Required in V1, Required in V2):

In terms of procedure, this scanning step is identical to step 1, however in this step, the prepared teeth are scanned. The contour of the actual preparation in FIG. 4 is C400. For the sake of simplicity in the figure, it is identical with that of the virtual preparation C102, but this need not be the case.

Step 10: Segment Prepared Teeth from Gingiva (Optional in V1, Optional in V2):

The segmentation of teeth and gingival in the prepared model can be executed analogously to step 2, but applied to the prepared model instead of the pre-prepared model. If this step is skipped, models 400 and 401 are identical.

Step 11: Align (Required in V1, Required in V2):

Logically and procedurally, this step is similar in variants V1 and V2; however this step relates to different models in either variant.

Figure 7:
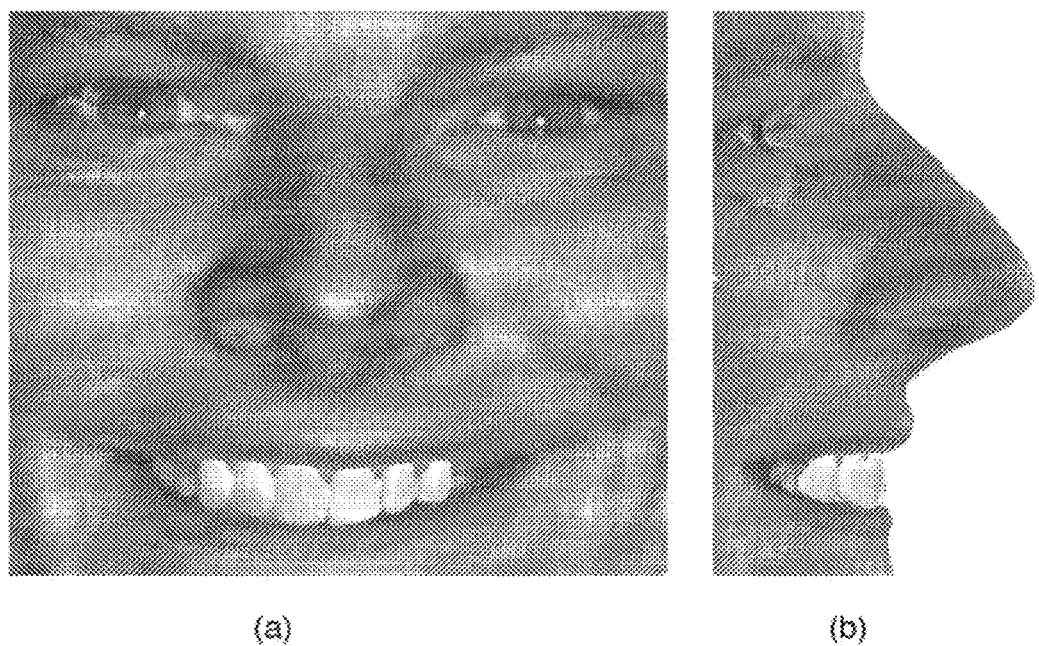
FIG. 7: Example screen snapshots of CAD software showing face model with part of the smile cut out and model of restoration (affecting teeth 6-11) and tissue (segmented) aligned to that of the face. For the sake of being able to distinguish face scan and restoration model in this Figure, the color of the restoration was intentionally not attempted matched that of the teeth in the face scan (this is visible even in the black-and-white pictures). (a): anterior view, (b): lateral view.

Variant V1:

Alignment of restoration designed for the pre-prepared teeth (step 6, model 101), prepared teeth (model 401) can be performed by the same software algorithms as described in step 3. Again, it is important to have some overlap in the models. Such areas will generally exist unless the preparation affects all teeth. The model of the restoration 300 is already in the same local coordinate system as model 101, based on which it was designed. Therefore, model 300 is also aligned with model 401 without any further processing. If the head/face scan (model 201) is available, it can be aligned to models 101/300 and 401 such that all three models match. FIG. 7 shows a typical result of this step 11 for such constellation.

Variant V2:

Alignment of prepared teeth (model 401) and the head/face scan (model 201) can be performed by the same software algorithms as described in step 3.

Step 12: Transfer Cad Design from Pre-Prepared to Prepared Teeth (Required in V1, not Applicable in V2):

Due to the manual preparation the actual preparation C402 (FIG. 5) will in general differ, at least slightly, from the virtual preparation C102 created in the design step 6. Thus, the restoration design needs to be modified accordingly, but preferably the transfer should maintain as much of the design created in step 6 as possible. This procedure is preferably implemented in software.

The automation provided by this step 12 is what lacks in the manual and subjective process that is the current state of technology. Typically today, to transfer the design, the dental technician looks at the original diagnostic wax-up and manually tries to replicate this design for the real restorations, incorporating potential comments from the dentist and the patient. This manual replication process is both costly, inaccurate, and time consuming.

Figure 5:
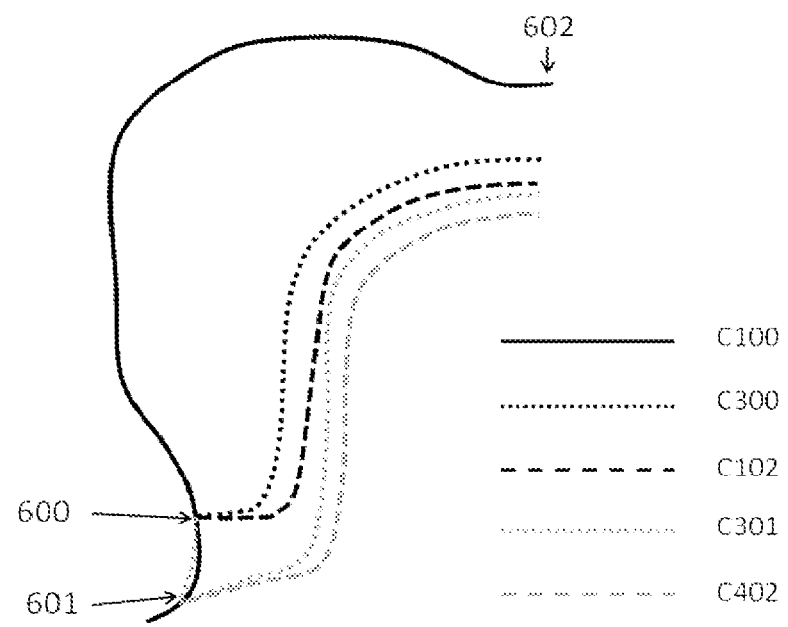
FIG. 5: Zoomed sagital section of a schematic tooth, illustrating step the transfer of the pre-preparation design to the prepared teeth.

A preferred algorithm for this step 12 starts by demarcating the margin line in both the virtual preparation (600 in FIG. 5) and the actual preparation (601 in FIG. 5). While the margins are points in the 2D cross section that is FIG. 5, in reality they are curves in 3D, and can for example be represented by (B-) splines. Dental CAD software like 3Shape's DentalDesigner can automatically detect margin lines and place said splines, but user interaction should also be allowed. The transformation between 600 and 601 is denoted T.

A free form deformation (FFD) model can used to generalize T to surfaces. This process is often also called "morphing". The morphing operation affects the near-margin portion of model 300, with decreasing impact for surface portions with decreasing distances from the margin. The relevant parameters of the algorithm can be adjusted by the user. A similar procedure for "crown matching" has been proposed in [8], however outside the scope of dental restorations. Colloquially speaking, morphing is like stretching a rubber balloon by pulling or pushing its "lips" (the thick ring through which the air is blown in, which corresponds to the margin line).

Note that in the example shown in FIG. 5, the prepared margin is located gingivally from the virtual one, so therefore the exterior surface of model 300 needs to be extended to arrive at model 301. The opposite case is however also possible. If the preparation ends up removing less material than assumed when creating model 300, the exterior surface of model 301 can be smaller than that of model 300. In other words, morphing can both be a contraction and a stretching operation. For a given tooth, morphing can even be a combination of contraction and stretching along various sections of the margin, namely when there are deviations between the virtual and actual preparation in both the gingival and the occusal/incisal direction.

Away from the margin towards the interior portions of the preparation/restoration, morphing need not be applied. Instead, the inner surface of the restoration can be computed in the normal fashion, i.e., the surface is created by an offset of the preparation above the margin line controlled by several parameters.

Away from the margin along the exterior of the restoration and beyond the radius of influence of the morphing operation (section 600 to 602 in FIG. 5), the surfaces of pre-prepared design and final design are identical, i.e. contours C300 and C301 overlay each other.

By combining the identical, the morphed, and the preparation-generated surface the final CAD design 301 (contour C301) is completed. When creating the final CAD design, material and manufacturing process requirements should be included, e.g. the actual design can be split into two files for pressing. If step 7 was skipped and thus model 102 is not truly available (it is the same as model 101), the virtual margin line can also be taking from the model of the restoration 300.

Further modifications to the design of the restoration can be made with the same procedures as mentioned under step 6. If color was adjusted in step 6, it may be advantageous to transfer the color information to the design and later manufacture of the restoration.

Only in the unlikely event of the actual preparation matching the virtual one, and no other modifications being desirable, will models 300 and 301 be identical.

Step 13: Produce (Optional in V1, Optional in V2):

Once model 301 has been finalized, it can be produced using CAM (Computer Aided Manufacturing). Both rapid prototyping (RP) machines and milling machines can be used for the actual production. A CAM software (e.g. 3Shape CAMbridge) prepares the data (including model 301) for production. For RP machines this preparation typically involves 3D rotation, placement (nesting), supports, slicing, ID-tags, etc. For milling machines the preparation typically involves 3D rotation, placement (nesting), sprues (connector pins), drops, engraving, milling path generation and post processing, etc. Some dental CAD/CAM solutions include the same internal steps of preparation for production and are thus technically suitable for the method described in this invention, but are currently not open to 3D models generated by other manufacturers' equipment (e.g., Sirona CEREC).

The production process can either manufacture the restoration immediately (e.g., from blocks of zirconia), or indirectly. In the indirect process, for example wax is milled or printed and then cast using traditional "lost wax" techniques. Many manufacturers offer RP (SLA, SLS, SLM, DLP, FDM, Polyjet, etc.) and/or milling machines suitable for such work, e.g., Roland, 3DSystems, EnvisionTec, Solidscape, DWS, EOS, ProMetal, and others.

Manufacturing may in many cases be performed at another location than the preceding steps. Digital models and designs can for example be transferred to a processing center via the internet.

Although some embodiments have been described and shown in detail, the invention is not restricted to them, but may also be embodied in other ways within the scope of the subject matter defined in the following claims. In particular, it is to be understood that other embodiments may be utilised and structural and functional modifications may be made without departing from the scope of the present invention.

In device claims enumerating several means, several of these means can be embodied by one and the same item of hardware. The mere fact that certain measures are recited in mutually different dependent claims or described in different embodiments does not indicate that a combination of these measures cannot be used to advantage.

It should be emphasized that the term "comprises/comprising" when used in this specification is taken to specify the presence of stated features, integers, steps or components but does not preclude the presence or addition of one or more other features, integers, steps, components or groups thereof.

The features of the method described above and in the following may be implemented in software and carried out on a data processing system or other processing means caused by the execution of computer-executable instructions. The instructions may be program code means loaded in a memory, such as a RAM, from a storage medium or from another computer via a computer network. Alternatively, the described features may be implemented by hard-wired circuitry instead of software or in combination with software.

REFERENCES

[1] Ackerman M B, Ackerman J L. Smile analysis and design in the digital era. J Clin Orthod. 2002; 36, 221-36.
[2] Xia J, Wang D, Samman N, Wai R, Yeung K, Tideman H. Computer-assisted three-dimensional surgical planning and simulation: 3D color facial model generation. Int J Oral & Maxillofacial Surgery 2002, 29 (1), 2-10.
[3] Rangel F A, Maal T J, Bergé S J, van Vlijmen O J, Plooij J M, Schutyser F, Kuijpers-Jagtman A M. Integration of digital dental casts in 3-dimensional facial photographs. Am J Orthod Dentofacial Orthop. 2008, 134 (6), 820-6.
[4] Callieri M, Cignoni P, Scopigno R. Reconstructing textured meshes from multiple range+rgb maps. VMV 2002, Erlangen, Nov. 20-22, 2002.
[5] Zhao B, Ong S H, Foong K W C. Multimodal Registration of Dental and Facial Images. Proc (444) Signal and Image Processing. Hawaii, Aug. 23-25, 2004.
[6] Ahmad I: Anterior dental aestethic: Facial perspective. Brit Dental J 2005, 199 (1), 15-21.
[7] Xia J, Samman N, Yeung R W, Wang D, Shen S G, Ip H H, Tideman H. Computer-assisted three-dimensional surgical planning and simulation. 3D soft tissue planning and prediction. Int J Oral Maxillofac Surg. 2000 29 (4), 250-8.
[8] Hassana H, El-Baza A, Faraga A A, Farmanb A G, Tasmanb S, Millera W M. A volumetric 3D model of the human jaw, CARS 2005: Computer Assisted Radiology and Surgery 2005. 1244-1249. doi:10.1016/j.ics.2005.03.345

[9] Pinheiro A P, Andrade A O, Pereira A A, Bellmo D. A computational method for recording and analysis of mandibular movements. J Appl Oral Sci. 2008; 16 (5): 321-7

The invention claimed is:

1. A method for planning, visualizing, and/or optimizing dental restoration on at least a part of pre-prepared teeth of a patient, wherein said method comprises:
    obtaining a first 3D digital model of at least a part of the pre-prepared teeth, said first 3D digital model comprising a first portion expressing the shape of one or more teeth prior to preparation of the one or more teeth;
    designing at least one dental restoration CAD model for said one or more teeth based on the first portion of the first 3D digital model of at least a part of the pre-prepared teeth;
    obtaining a second 3D digital model of at least a part of the prepared teeth, where the prepared teeth are provided by preparing the pre-prepared teeth by dental restorative work; and
    aligning the first 3D digital model of the pre-prepared teeth and the second 3D digital model of the prepared teeth.

2. The method according to claim 1, comprising designing a dental preparation CAD model, at least partly based on the first portion of the first 3D digital model of the pre-prepared teeth.

3. The method according to claim 2, further comprising providing a preparation guide for the dentist prior to preparing the teeth, said preparation guide at least partly based on the dental preparation CAD model.

4. The method according to claim 3, wherein said preparation guide comprises instruction text, multiple 2D screen shoots, 3D animations, computer visualization, videos and/or instructions for machined/robot preparation.

5. The method according to claim 2, further comprising transferring the design of the dental restoration CAD model to the second 3D digital model of the prepared teeth.

6. The method according to claim 5, wherein transferring the design of the dental restoration CAD model comprises aligning the dental preparation CAD model with the second 3D digital model of the prepared teeth.

7. The method according to claim 5, wherein transferring the design of the dental restoration CAD model comprises morphing part of the dental restoration CAD model to the second 3D digital model of the prepared teeth, where morphing is applied near the margin line of the dental restoration CAD model and/or the second 3D digital model of the prepared teeth.

8. The method according to claim 7, wherein morphing results in a change that is highest near the margin line of the dental restoration CAD model and/or the second 3D digital model of the prepared teeth, with decreasing change when increasing the distance to the margin line.

9. The method according to claim 5, wherein transferring the design of the dental restoration CAD model comprises creating an inner surface of the dental restoration CAD model as an offset to the second 3D digital model of the prepared teeth, said offset starting from the margin line of the second 3D digital model of the prepared teeth in the occlusal/incisal direction.

10. The method according to claim 5, wherein a part of the outer surface of the dental restoration CAD model is maintained when transferred to the second 3D digital model of the prepared teeth, the contour of the inner surface of the dental restoration CAD model is similar to the outer surface of the second 3D digital model of the prepared teeth and the margin line area of the dental restoration CAD model and the second 3D digital model of the prepared teeth are morphed together.

11. The method according to claim 5, wherein the step of transferring the design of the dental restoration CAD model comprises morphing the dental preparation CAD model with the second 3D digital model of the prepared teeth, thereby providing a transformation of the dental preparation CAD model to the second 3D digital model of the prepared teeth, and subsequently applying this transformation to the dental restoration CAD model.

12. The method according to claim 5, comprising modifying the design of the dental restoration CAD model subsequent to the step of transferring said dental restoration CAD model to the second 3D digital model of the prepared teeth.

13. The method according to claim 1, said method further comprising
    providing a facial 3D digital model of the patient, with at least a part of the teeth being visible, where the facial 3D scan is provided by means of optically scanning at least a part of the face of the patient;
    at least partly aligning the first 3D digital model of the pre-prepared teeth and/or the dental restoration CAD model with the visible teeth in the facial 3D digital model; and
    at least partly designing the dental restoration CAD model based on the facial 3D digital model.

14. The method according to claim 13, comprising cutting and/or removing at least a part of the teeth from the 3D digital facial model.

15. The method according to claim 13, comprising visualizing the dental restoration CAD model aligned in the facial 3D digital model.

16. The method according to claim 13, comprising at least partially segmenting teeth and tissue in the facial 3D digital model.

17. The method according to claim 1, wherein preparing the pre-prepared teeth by dental restorative work is at least partly based on the dental restoration CAD model.

18. The method according to claim 1, wherein the dental restoration CAD model is visualized side-by-side, along and/or on top of the first 3D digital model of the pre-prepared teeth.

19. The method according to claim 1, comprising at least partially segmenting teeth and tissue, such as gingival, in the first 3D digital model of the pre-prepared teeth and/or in the second 3D digital model of the prepared teeth.

20. The method according to claim 1, wherein the dental restoration can be one or more inlays, onlays, veneers, crowns, bridges or combinations thereof and/or the dental restoration can be a removable partial denture framework and/or an implant-retained structure.

* * * * *